United States Patent
Behl et al.

[19]

[11] Patent Number: 6,077,261

[45] Date of Patent: *Jun. 20, 2000

[54] DEVICE FOR PERMANENT VESSEL OCCLUSION

[75] Inventors: Robert S. Behl, Palo Alto; Thomas Palermo, San Jose; Colin J. Nichols, Fremont, all of Calif.

[73] Assignee: Radiotherapeutics Corporation, Sunnyvale, Calif.

[*] Notice: This patent is subject to a terminal disclaimer.

[21] Appl. No.: 09/001,968

[22] Filed: Dec. 31, 1997

Related U.S. Application Data

[63] Continuation of application No. 08/488,444, Jun. 7, 1995, Pat. No. 5,709,224.

[51] Int. Cl.[7] .................................................. A61B 17/36
[52] U.S. Cl. ............................... 606/50; 606/51; 606/216
[58] Field of Search .................................. 607/27, 32, 41, 607/42, 45, 52, 8, 191, 192, 194, 213, 216, 46, 50, 51, 157, 158; 307/100–102

[56] References Cited

U.S. PATENT DOCUMENTS

| | | |
|---|---|---|
| 1,814,791 | 7/1931 | Ende . |
| 1,908,583 | 5/1933 | Wappler . |
| 1,943,543 | 1/1934 | McFadden . |
| 1,995,526 | 3/1935 | Wappler . |
| 2,022,065 | 11/1935 | Wappler . |
| 3,100,489 | 8/1963 | Bagley . |
| 3,868,956 | 3/1975 | Alfidi et al. . |
| 4,005,714 | 2/1977 | Hiltebrandt . |
| 4,011,872 | 3/1977 | Komiya . |
| 4,041,952 | 8/1977 | Morrison, Jr. et al. . |
| 4,209,018 | 6/1980 | Meinke et al. . |
| 4,492,231 | 1/1985 | Auth . |
| 4,582,057 | 4/1986 | Auth et al. . |
| 4,655,216 | 4/1987 | Tischer . |
| 4,685,459 | 8/1987 | Koch et al. . |
| 4,994,069 | 2/1991 | Ritchart et al. . |
| 5,108,407 | 4/1992 | Geremia et al. . |
| 5,122,136 | 6/1992 | Guglielmi et al. . |
| 5,217,484 | 6/1993 | Marks . |

(List continued on next page.)

FOREIGN PATENT DOCUMENTS

| | | |
|---|---|---|
| 25 40 968 A1 | 3/1977 | Germany . |
| 26 46 228 A1 | 4/1978 | Germany . |
| 41 39 029 A1 | 6/1993 | Germany . |
| 2-121675 | 5/1990 | Japan . |
| WO 93/01758 | 2/1993 | WIPO . |
| WO 93/06884 | 4/1993 | WIPO . |
| WO 94/06503 | 3/1994 | WIPO . |
| WO 94/09705 | 5/1994 | WIPO . |

(List continued on next page.)

OTHER PUBLICATIONS

Becker, C. D. et al. "Long–Term Occlusion of the Porcine Cystic Duct by Means of Endoluminal Radio–Frequency Electrocoagulation" (1988) *Radiology* 167:63–68.

Becker, C. D. et al. "Catheter for Endoluminal Bipolar Electrocoagulation" (1989) *Radiology* 170:561–562.

Brunelle, F. et al. "A Bipolar Electrode for Vascular Electrocoagulation with Alternating Current" (1980) *Technical Notes* 137:239–240.

(List continued on next page.)

*Primary Examiner*—John P. Leubecker
*Attorney, Agent, or Firm*—Townsend and Townsend and Crew LLP

[57] ABSTRACT

Body lumens such as blood vessels are selectively occluded by mechanically collapsing the blood vessel and subsequently applying energy or other occlusive conditions within or adjacent the collapsed region. For example, vessel collapsing mechanisms can include spreadable opposed elements, reciprocating jaw mechanisms having penetrating elements, and devices for applying negative pressure to collapse the blood vessel. One or more electrodes can be used in a monopolar or bipolar fashion to apply radiofrequency or other energy to the body lumen in the region where it has been collapsed.

12 Claims, 8 Drawing Sheets

U.S. PATENT DOCUMENTS

| | | |
|---|---|---|
| 5,226,911 | 7/1993 | Chee et al. . |
| 5,234,437 | 8/1993 | Sepetka . |
| 5,250,071 | 10/1993 | Palermo . |
| 5,261,916 | 11/1993 | Engelson . |
| 5,281,216 | 1/1994 | Klicek . |
| 5,303,719 | 4/1994 | Wilk et al. . |
| 5,312,415 | 5/1994 | Palermo . |
| 5,364,389 | 11/1994 | Anderson . |
| 5,364,393 | 11/1994 | Auth et al. . |
| 5,366,490 | 11/1994 | Edwards et al. . |
| 5,385,544 | 1/1995 | Edwards et al. . |
| 5,403,311 | 4/1995 | Abele et al. . |
| 5,405,322 | 4/1995 | Lennox et al. . |
| 5,415,657 | 5/1995 | Taymor-Luria . |
| 5,437,664 | 8/1995 | Cohen et al. . |
| 5,507,744 | 4/1996 | Tay et al. . |

FOREIGN PATENT DOCUMENTS

| | | |
|---|---|---|
| WO 94/10936 | 5/1994 | WIPO . |
| WO 94/11051 | 5/1994 | WIPO . |
| WO 95/02366 | 1/1995 | WIPO . |

OTHER PUBLICATIONS

Brunelle, F. et al. "Endovascular Electrocoagulation with a Bipolar Electrode and Alternative current: A Follow–up Study in Dogs" (1983) *Radiology* 148:413–415.

Cragg, A.H. et al. "Endovascular Diathermic Vessel Occlusion," (1982) *Radiology* 144:303–308.

Tanigawa, N. et al. "Intraarterial Occlusion by Radiofrequency" (1994) Acta Radiologica ISSN 0248–1851 pp. 626–628.

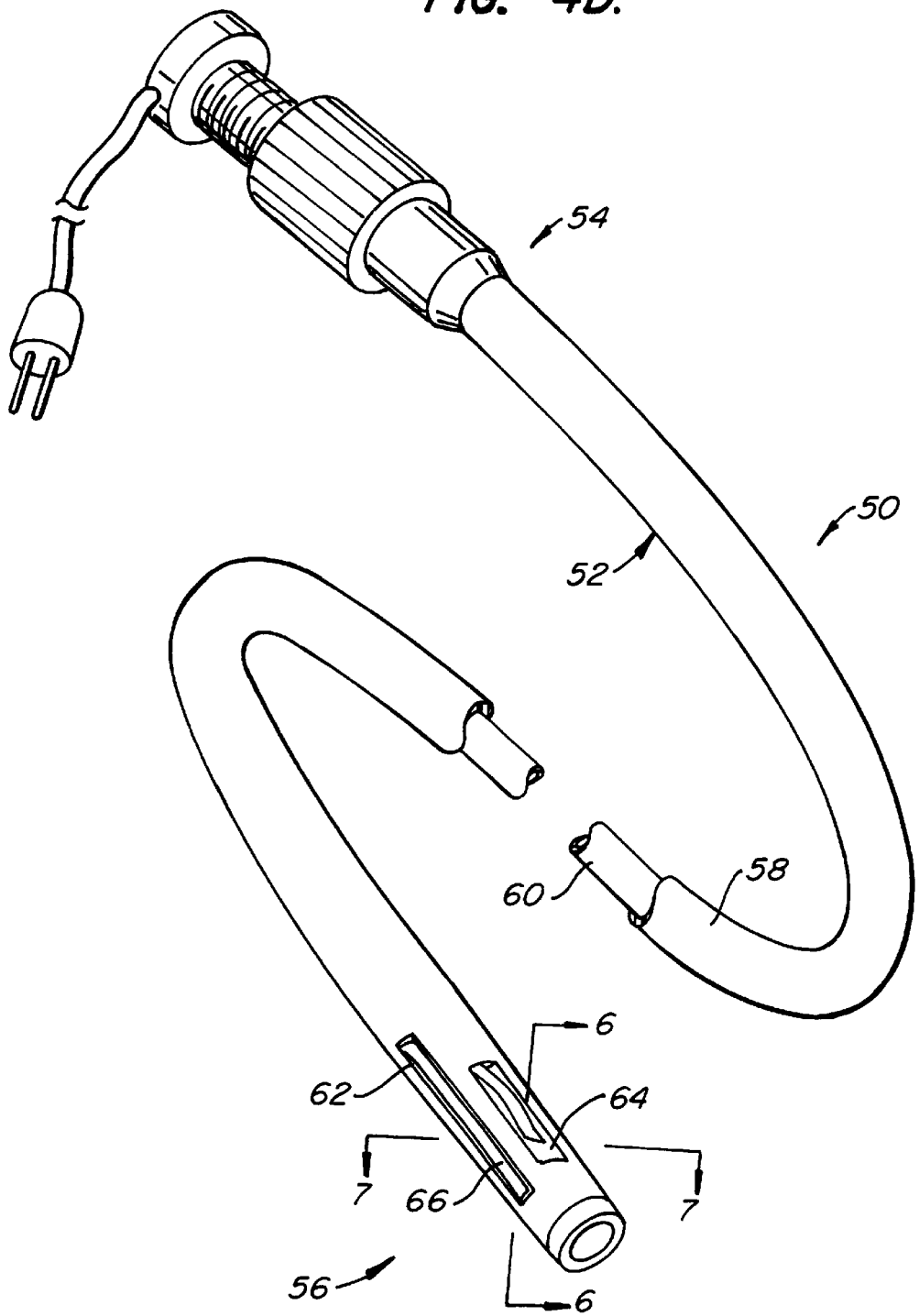

DEVICE FOR PERMANENT VESSEL OCCLUSION

This application is a continuation of application Ser. No. 08/488,444, filed on Jun. 7, 1995, now U.S. Pat. No. 5,709,224 the full disclosure of which is incorporated herein by reference.

BACKGROUND OF THE INVENTION

1. Field of the Invention

The present invention relates generally to methods and devices for the selective occlusion of body lumens. More particularly, the present invention relates to the methods and devices for drawing opposed portions of the body lumen wall together and subsequently fusing regions of said opposed portions which are in contact with each other together.

The selective occlusion of blood vessels in a patient is a part of many modern therapeutic treatments, including the control of internal bleeding, the occlusion of blood supply to tumors, the isolation of diseased body organs prior to removal, the relief of blood pressure in a region of aneurism, and the like. While such procedures rely generally on the blockage of arteries, the selective occlusion of veins is also useful in procedures such as veiniotomy.

The selective occlusion of blood vessels can be achieved by a variety of specific techniques. Such techniques fall generally into two categories. First, chemical occlusion of blood vessels is typically accomplished by introduction of a non-physiologic solution into the vessel lumen. The solution is selected to destroy the vessel lining and injure the underlying tissue, causing edema, fibrin deposition, and eventually fibrosis of the lumen. In addition to the use of such chemical agents, e.g., ethanol, tetradecyl sulfate, and hypertonic saline, heat can also be applied to induce fibrosis of the lumen.

The second general approach for vessel occlusion is mechanical. For example, in open surgical and endoscopic procedures, the body vessel can be externally clamped and radiofrequency energy applied. While the external procedures can be very effective, it requires external access to the lumen and is unsuitable for endoluminal techniques.

Mechanical endoluminal techniques for selective vessel occlusion are also in use. Such techniques include the use of detachable balloons, embolic coils, and the like to physically block the vessel lumen. Detachable balloons, however, are difficult to deliver and usually not suitable for permanent implantation. Embolic coils are difficult to position, difficult to size for a particular site within a vessel lumen, frequently migrate from the point of initial implantation, and sometimes fail to initiate thrombosis or fibrosis in order to permanently occlude the lumen.

The use of chemical occlusion techniques is also problematic. Chemical occlusion is not readily employed in blood vessels having a high flow rate since the chemical agents are quickly diluted. Moreover, the chemical agents used can cause injury if leakage occurs away from the desired treatment site. Even when the chemical agent is properly released, some individuals can experience systemic toxicity.

Of particular interest to the present invention, the use of monopolar and bipolar radiofrequency devices has been proposed for the endoluminal occlusion of body vessels. For example, U.S. Pat. No. 5,403,311, describes occlusion of a body lumen using electrosurgical electrodes which are transcutaneously positioned within the lumen. Catheters for radiofrequency injury and occlusion of the cystic duct are described in Becker et al. (1989) RADIOLOGY 170:561–562 and (1988) RADIOLOGY 167:63–68. Methods and catheters for electrosurgical endovascular occlusion are described in Brunelle et al. (1980) RADIOLOGY 137:239–240; Cragg et al. (1982) RADIOLOGY 144:303–308; and Brunelle et al. (1983) RADIOLOGY 148:413–415. Such techniques, however, have not generally been useful in large blood vessels.

For these reasons, it would be desirable to provide improved methods and devices for the selective occlusion of body lumens, and particularly of blood vessels, for use in the procedures described above. Such methods and devices should permit the endoluminal occlusion and sealing of body lumens, being effective with large body lumens as well as being suitable for accessing and closure of small body lumens. The methods and devices should provide for relatively immediate occlusion of the vessel, thus permitting occlusion to be radiologically verified at the end of the procedure. The occlusions thus achieved should be permanent and not be dependent on the implantation of coils, balloons, embolization particles, or other devices. Preferably, however, it will be possible to test the occlusion, e.g. observe the result of occlusion of blood flow in a vessel, prior to permanent occlusion of the lumen. Additionally, it would desirable if such methods and devices permitted the formation of multiple occlusions of the same vessel, or single or multiple occlusion of different vessels, during a single procedure, preferably during a single endoluminal introduction of the device.

2. Description of the Background Art

Methods and devices for implanting vasoocclusive elements, such as coils, in blood vessels and other lumen are described in U.S. Pat. Nos. 5,312,415; 5,261,916; 5,250,071; 5,234,437; 5,226,911; 5,217,484; 5,122,136; 5,108,407; 4,994,069; and 3,868,956; and published PCT applications WO 94/11051; WO 94/10936; WO 94/09705; WO 94/06503; and WO 93/06884. Some of the devices described in the above listed patents and published applications suggest passing electrical current through the element to enhance blood clotting.

Electrosurgical probes for electrosurgical, electrocautery, and other procedures are described in U.S. Pat. Nos. 5,405,322; 5,385,544; 5,366,490; 5,364,393; 5,281,216; 4,685,459; 4,655,216; 4,582,057; 4,492,231; 4,209,018; 4,041,952; 4,011,872; 4,005,714; 3,100,489; 2,022,065; 1,995,526; 1,943,543; 1,908,583; and 1,814,791; and published Japanese application 2-121675; published German applications DE 4139029; DT 2646228; and DT 2540968; and published PCT applications WO 95/02366 and WO 93/01758. In particular, U.S. Pat. No. 5,405,322 discloses a dual balloon catheter having a radiofrequency current source with means for evacuating blood from between the balloons, and U.S. Pat. No. 4,011,872 discloses bipolar graspers which can grasp and excise tissue.

See also the patent and publications described in the Field of the Invention above.

SUMMARY OF THE INVENTION

Methods and apparatus are provided for selectively occluding body lumens, such as blood vessels, by first drawing opposed portions of the lumen wall together over an occlusion region (to slow blood flow in the case of blood vessels), and thereafter at least partially sealing the opposed portions of the wall together while they are being held in contact by a force applied from within the lumen. The sealing step normally comprises injuring the lumenal wall to initiate clotting and subsequent fibrosis to permanently occlude the lumen, usually by initiating a radiofrequency current flow through the wall region. In some cases however, injury could be induced by the application of chemical agents, heat, or other energy sources. The method preferably comprises advancing a probe through the body lumen to a target site, applying a force through the probe to at least partially draw the opposed lumen portions together over an occlusion region, and positioning at least one electrode on the probe proximate to (i.e., in or near) the occlusion region. By then initiating a radiofrequency current flow from the probe through the occlusion region of the lumen, the lumenal wall will be injured, resulting in closure of the lumen. In particular, in the case of blood vessels, fusion will occur at least partially through thrombosis and fibrosis, where the initial blockage of blood flow resulting from mechanical closure of the lumen greatly accelerates such processes.

The probe, which is typically in the form of an intravascular catheter which can be percutaneously introduced via well-known procedures, is advanced to the target site in a body lumen in a known manner, typically over a guide wire. The force which draws opposed portions of the lumen wall together can be applied by any of a number of techniques. In a preferred example, the force is applied by spreading a pair of opposed elements in a radially outward direction from the distal end of the probe proximate the at least one electrode. The outward movement of the opposed elements will flatten the blood vessel in a desired manner. Alternatively, the probe can utilize a pair of reciprocatable jaws having distal penetrating elements. By opening the jaws, engaging the vessel wall with the penetrating elements, and closing the jaws, the lumen wall can be flattened or pinched closed (and optionally the penetrating elements can act as bipolar electrodes in applying the radiofrequency current flow). The lumen-closing force can also be applied by drawing a negative pressure through the probe to collapse the blood vessel lumen. Usually, the negative pressure can be drawn while the vessel is occluded by a proximal balloon, or by either the opposed elements or the reciprocatable jaw elements described above. In the latter cases, provision of a negative pressure will enhance the closure effected by the mechanical closing means.

The at least one electrode can be engaged against the lumen wall in a variety of ways. For example, the electrode (and optionally a pair of electrodes for bipolar operation) can simply be disposed at a location on the probe which will be located near the occlusion region in the vessel lumen when the lumen wall is drawn closed. Alternatively, the electrode may be provided by a separate member, such as a conventional or specialized guide wire which lies insulated within the catheter body which extends into the closed region of the blood vessel wall while the radiofrequency current flow is being initiated. In the latter case, the guide wire can act as the active electrode, while a dispersive electrode is located on the probe or externally to the patient. As yet another alternative, a pair of bipolar electrodes can be provided as the penetrating elements on the reciprocatable jaw device described above. A variety of other specific designs could also be employed so long as the electrode can be brought near or within the closed region of the body lumen while the radiofrequency current flow is being initiated.

Devices according to the present invention will generally comprise a shaft having a proximal end and a distal end. For vascular applications, the shaft will typically be a tubular catheter body capable of being introduced to the vascular system over a guide wire in a conventional manner. A mechanism will be provided on the shaft for engaging the interior wall of a treated body lumen in order to draw opposed portions of the wall together over an occlusion region. The shaft will further include a mechanism for heating the opposed wall portions over the occlusion region, typically comprising electrodes for applying radiofrequency current through the tissue, but alternatively comprising heat-applying means, chemical agent-applying means, or the like. In a first embodiment, the lumen-closing mechanism comprises a pair of opposed elements which can also comprise spread apart members to flatten the lumen along a transverse line defined by said elements. The lumen-closing mechanism can also comprise opposed, penetrating elements which can be selectively opened and closed to engage and draw together the wall portions. Usually, the opposed elements will be openable jaws, each having a reciprocatably mounted pin selectively penetrating the vessel wall. The lumen can then be closed by opening the jaws to engage (and in some cases spread) the lumenal wall, penetrating the pins into the lumen wall, and closing the jaws.

The radiofrequency heating means typically comprises at least one active electrode, and usually at least two electrodes, where the second electrode can be either a second bipolar electrode or a dispersive electrode (where the first electrode will function in a monopolar manner). The electrodes are thus utilized to apply monopolar or bipolar radiofrequency energy to the occlusion region within the vessel lumen. Frequently, the electrode(s) will be associated with the vessel-closing elements. For example, the opposed spreading elements can also define the treatment electrodes on the probe. Alternatively, separate radiofrequency current-supplying electrodes can be provided on the probe. For example, a separate guide wire can be provided as a monopolar or bipolar electrode. Alternatively, separate bipolar active and/or dispersive electrodes can be mounted on the probe body in the region of the vessel-closing elements.

BRIEF DESCRIPTION OF THE DRAWINGS

FIGS. 4A–4D illustrate the use of the device of FIG. 1 and a method for occluding a blood vessel according to the principles of the present invention.

FIG. 5 is a perspective view of a second embodiment of a lumen occlusion device constructed in accordance with the principles of the present invention.

DESCRIPTION OF THE SPECIFIC EMBODIMENTS

Figure 1:
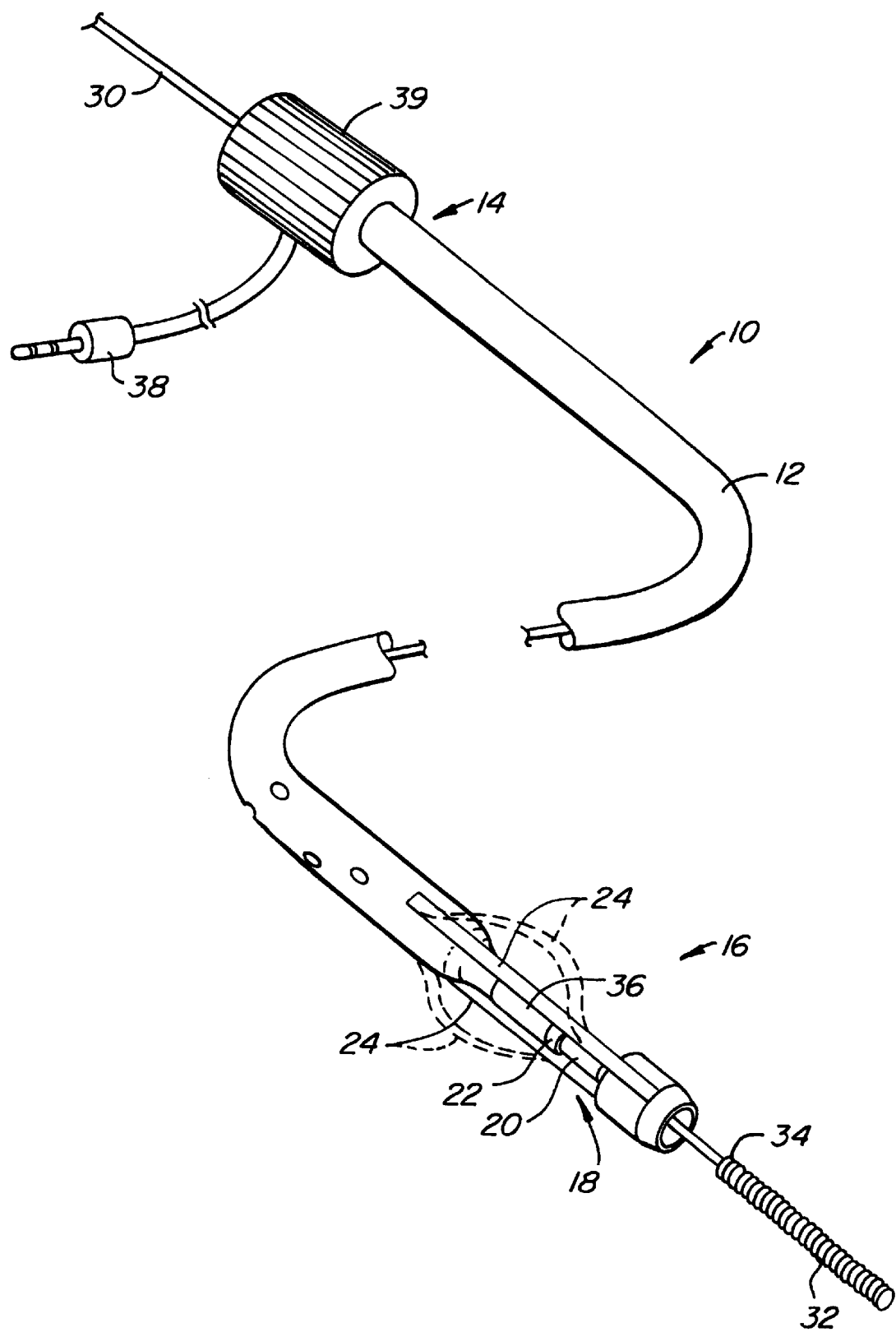
FIG. 1 is a perspective view of a first embodiment of a lumen occlusion device constructed in accordance with the principles of the present invention.

The methods and devices of the present invention will be useful for selectively occluding virtually any body lumen having a luminal wall that can be mechanically closed followed by the application of energy or other conditions which to injure the vessel to cause permanent closure and luminal occlusion. While the present invention will find its greatest use in the selective occlusion of blood vessels, including both arteries and veins, it will also find use with other body lumens, such as the fallopian tubes, ureter, bile duct, and the like.

In the case of blood vessel occlusion, the lumen will be mechanically closed to bring opposed portions of the endothelial wall of the blood vessel partially or totally together, and energy applied to the occlusion region between said opposed wall portions. The energy will injure or destroy the endothelial cells and underlying tissue in the occlusion region, thus initiating a process of thrombosis and fibrosis which will result in relatively rapid vessel occlusion. In many cases, the vessel closure will be substantially complete within a very short time, typically 10 minutes or less, usually 5 minutes or less, and often 1 minute or less. In other cases, such as when one or more electrodes are initially positioned within the occlusion region, complete closure of the vessel may take a longer time period, frequently as long as 1 hour, sometimes as long as 3 hours. Exemplary treatment times (during which current flow is applied) are in the range from 5 seconds to 4 minutes, usually from 10 seconds to 1 minute.

A particular advantage of the present invention is that by mechanically closing the vessel to occlude the vessel lumen, blood flow is substantially slowed or stopped, greatly enhancing the rate of thermal transfer, which in turn enhances the rate of fibrosis and thrombosis. Even in the case where a small residual lumen remains after the device is removed, complete closure of the remaining area of the lumen will occur relatively rapidly. Initial mechanical (non-permanent) occlusion of the blood vessel is also an advantage since it permits confirmation that the site of occlusion is proper. That is, the physician can observe the effects of vessel occlusion (e.g. by radiography) prior to permanent occlusion.

Closure of the opposed wall portions in the occlusion region will usually be effected by the application of energy, such as heat energy, laser energy, electrical energy, or the like. Preferably, the energy source will be radiofrequency electrical energy, such as that supplied by conventional electrosurgical power supplies, such as those available from commercial vendors, including Valleylab, Aspen., Bovie, and Birtcher. The power supply will usually provide energy at frequencies from 200 kHz to 1.25 MHz, and may employ a conventional sinusoidal or non-sinusoidal wave form. The current provided will usually be in the range from 50 mA to 1 A, with the actual current depending primarily on vessel size, i.e. larger vessels will usually require higher currents. As discussed in more detail in connection with the specific embodiments below, the RF current may be applied in a monopolar or a bipolar fashion in or near the occlusion region. By "monopolar" it is meant that current flow will pass between (1) one or more "active" electrodes on the probe which have areas and configurations which concentrate the energy flux in order to have an injurious effect on the surrounding tissue and (2) a "dispersive" electrode which is located remotely from the active electrode(s) and which has a sufficiently large area so that the current density is low and non-injurious to surrounding tissue. In some cases, the dispersive electrode may be on the same probe as the active electrode, and in other cases, the dispersive electrode may be attached externally to the patient, e.g., using a contact pad placed on the patient's flank.

Bipolar devices according to the present invention will generally employ a pair of electrodes in close proximity each having an area and geometry selected to increase current density sufficient to injure or have other desired physiologic effect on adjacent tissue. In the case of bipolar devices, one or more electrodes will be connected to each pole of the radiofrequency power supply. Thus, the current flow in the occlusion region will be concentrated through tissue located between electrode pair(s), rather than from one or more electrodes to a remote, dispersive electrode (which is the case in monopolar operation).

Devices according to the present invention will comprise a probe, typically including a shaft having a proximal end and a distal end. For vascular applications, the shaft may be in the form of a conventional catheter body, typically having a length in the range from 40 cm to 200 cm, usually from 75 cm to 120 cm. The catheter body will usually include means for introducing the body over a movable guide wire, typically having a guide wire lumen running through at least a distal portion of the catheter body. Thus, the catheter body can have either conventional "over-the-wire" design where a movable guide wire is received through the entire length of the catheter body or may have a "rapid exchange" or "monorail" design where the guide wire is received through a lumen which extends only over a distal length of the body, typically from 5 cm to 25 cm. The catheter body will have an outside diameter consistent with its intended use, typically being from 1 mm to 5 mm, usually from 2 mm to 4 mm.

The catheter body may be formed from a variety of conventional catheter materials, including natural and synthetic polymers, such as polyvinyl chloride, polyurethanes, polyesters, polyethylenes, polytetrafluoroethylenes (PTFE's), nylons, and the like. The catheter bodies may optionally be reinforced to enhance their strength, torqueability, and the like. Exemplary reinforcement layers include metal fiber braids, polymeric fiber braids, metal or fiber helical windings, and the like. Optionally, a portion of the catheter body could be formed from a metal rod or hypo tube, particularly when the catheter body is a rapid exchange or monorail design.

The lumen occlusion device will also include at least one electrode for initiating radiofrequency current flow, as described above. The electrode may be disposed on the shaft, may be part of the vessel closing means (described below), and/or may be associated with the guide wire used to introduce the shaft to the body lumen, usually a blood vessel. Configuration of the electrode element will vary depending on whether it is intended to be an "active" electrode or a "dispersive" electrode. Active electrodes will typically have relatively small areas, typically being below about 20 mm$^2$, usually being below about 10 mm$^2$. Dispersive electrodes will typically have a somewhat larger area, typically being greater than 50 mm$^2$ for probe-mounted dispersive electrodes and greater than 100 cm$^2$ for external dispersive pads.

The vessel-closing mechanism on the lumen occlusion device may take any form which mechanically flattens or otherwise pinches or occludes the vessel while the occlusion energy is being applied. In a preferred embodiment, the vessel-closing mechanism will comprise a pair of thin, opposed elements which may be spread apart to flatten the vessel by radially moving opposed wall portions apart. Alternatively, the vessel-closing mechanism can comprise spreadable jaws having penetrating elements which engage and close the vessel wall as the jaws are closed. As a second alternative, the vessel closing mechanism can employ negative pressure for collapsing the vessel wall. Specific examples of each of these approaches are described in more detail in connection with the figures below.

Figure 2:
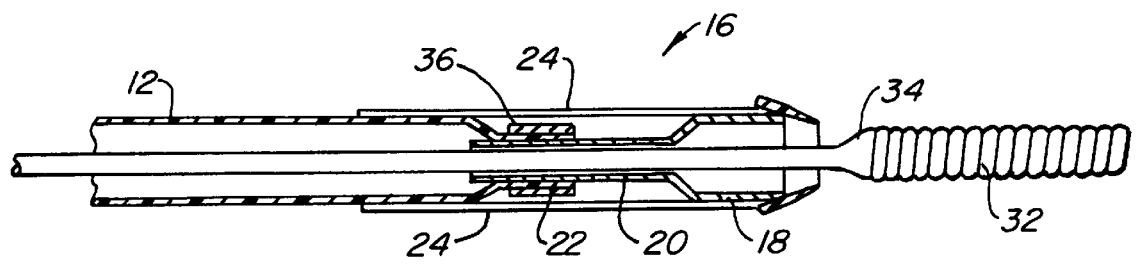
FIG. 2 is a detailed view of a distal end of the device of FIG. 1, shown in section with a pair of opposed vessel-closing elements shown in their collapsed (non-deployed) configuration.
Figure 3:
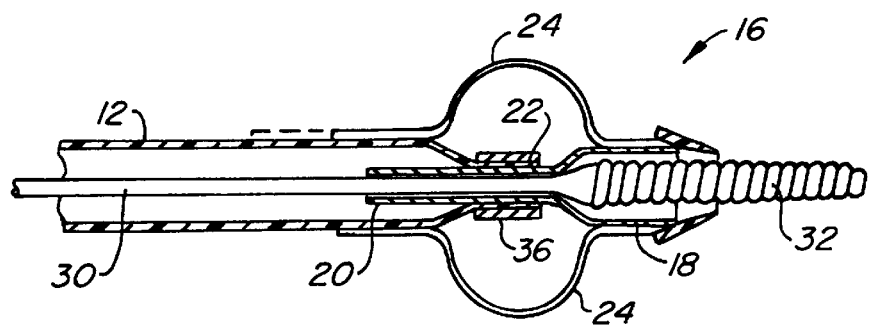
FIG. 3 is a view similar to FIG. 2, except that the opposed vessel-closing elements are shown in their spread-apart (deployed) configuration.

Referring now to FIGS. 1–3, a first lumen occlusion device 10 constructed in accordance with the principles of the present invention comprises a shaft in the form of a flexible catheter body 12 having a proximal end 14 and a distal end 16. A reciprocatable tip structure 18 has a reduced neck portion 20 which is reciprocatably received in a sleeve 22 formed on the body 12. A pair of opposed elements 24 are fixedly secured at the distal end of the catheter body 12 extending between the main portion of the body and the tip structure 18. By proximally translating the tip section 18 relative to the main portion of body 12, as illustrated in FIG. 3, the opposed elements 24 (which will be formed from a resilient material such as spring steel, superelastic alloy or plastic, or a resilient organic polymer) will bow in a radially outward direction.

The lumen occlusion device 10 further comprises a guide wire 30 having a tip 32 with an enlarged proximal end 34, as best seen in FIG. 2. Thus, the guide wire 34 may be proximally translated relative to the catheter body 12 (i.e., by pulling on the proximal end of the guide wire) in order to proximally translate tip structure 18 as illustrated in FIG. 3.

In this embodiment, guide wire 30 also serves as an active electrode for providing radiofrequency current flow in a monopolar procedure. The occlusion device 10 further includes a dispersive electrode 36 which may be conveniently mounted over the sleeve 22 (as illustrated) or alternatively at a proximal location on the catheter body 12. Of course, the dispersive electrode 36 could be located elsewhere on the catheter body, or it could be mounted separately from the catheter on the patient, e.g., by using an external dispersive plate which is mounted on the patient's skin. The dispersive electrode 36 and guide wire 30 may be connected to a suitable RF power supply (not shown) using a connector plug 38. Connection to the guide wire 30 can be completed using a bushing within the proximal housing 39, thus allowing relative rotation and translation.

Figure 4A:
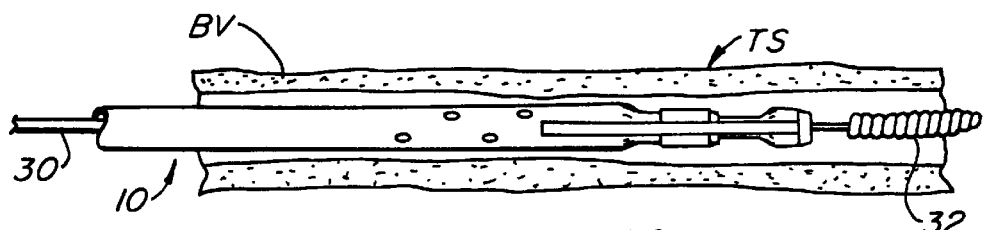

Use of the lumen occlusion device 10 is illustrated in FIGS. 4A–4D. The device 10 is introduced transluminally to a desired target site TS within a blood vessel BV or other body lumen. Typically, the guide wire 30 will first be introduced to the target site TS in a conventional manner. Once in position, the catheter body 12 will be introduced over the guide wire 30 in a conventional "over-the-wire" manner until the distal end of the device 10 reaches the target site, as shown in FIG. 4A.

Figure 4B:
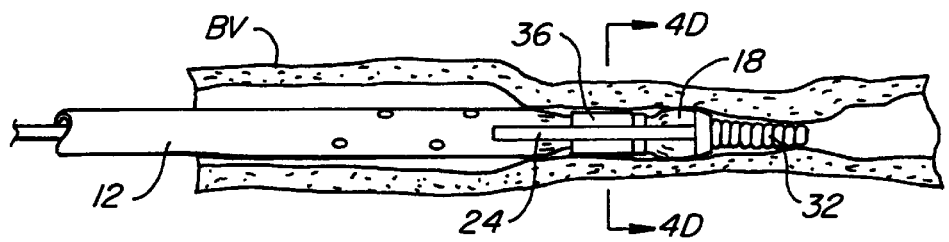
Figure 4C:
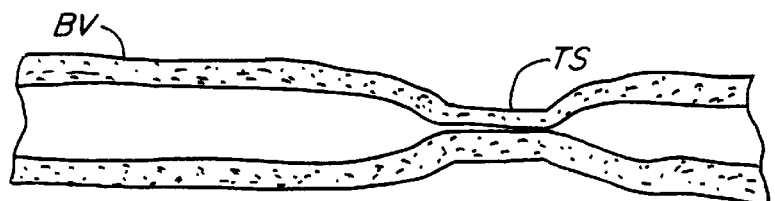

After reaching the target site TS, the guide wire 30 is pulled proximally (i.e., to the left, as illustrated in FIG. 4B) in order to proximally translate the tip structure 18 relative to the remainder of the catheter body 12. Such proximal translation of the tip structure 18 causes opposed members 24 to move radially outward and collapse the blood vessel, as illustrated in FIGS. 4B and 4D. After the blood vessel is collapsed, a radiofrequency current flow can be initiated between the guide wire tip 32 and the dispersive electrode 36, typically using a conventional radiofrequency power supply which is optionally modified to provide and optimum impedance match. After maintaining the radiofrequency current flow for a desired time and at a desired current level (as described previously), the device 10 will be withdrawn. At the time of device removal, the blood vessel will be highly thrombosed and totally or mostly occluded. A small lumen may remain in the region where guide wire tip 32 had been deployed. Any such remaining lumen, however, will quickly occlude by normal inflammatory and clotting processes, thus assuring the closure of the blood vessel BV at the target site TS, as shown in FIG. 4C. Over time, the thrombosed region will fibrose to form permanent sealing of the blood vessel or other body lumen.

A second embodiment 50 of the lumen occlusion device of the present invention is illustrated in FIGS. 5–8. The device 50 is similar to device 10 in that it includes the pair of spreadable, opposed elements for mechanically collapsing the blood vessel lumen. The device 50 differs from device 10, however, in that it includes a pair of deployable bipolar pins or electrodes, as will now be described in more detail.

The lumen occlusion device 50 includes a flexible catheter body 52 having a proximal end 54 and a distal end 56. The flexible catheter includes both an outer sheath 58 and an inner member 60, where the outer sheath and inner member are axially reciprocatable relative to one another. The outer sheath 58 includes a first pair of opposed slots 62 (best seen in FIG. 7) and a second pair of opposed slots 64 (best seen in FIG. 6). The first slots 62 are aligned with opposed members 66 which are attached between distal end 68 of the inner member 60 and the distal end of the outer sheath 58, as best observed in FIG. 7. The opposed elements 60 are similar to the opposed elements 24 of device 10, and distal translation of the inner member 60 relative to the outer sheath 58 will cause the members 66 to bow in a radially outward direction, as shown in broken line in FIG. 7.

Figure 6:
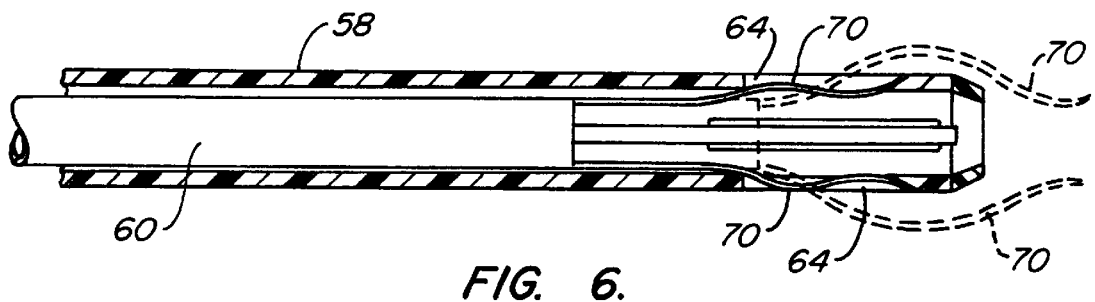
FIG. 6 is a detailed, cross-sectional view taken along line 6—6 of FIG. 5, shown with a pair of vessel-engaging electrodes in a retracted configuration (solid line) and a deployed configuration (broken line).
Figure 7:
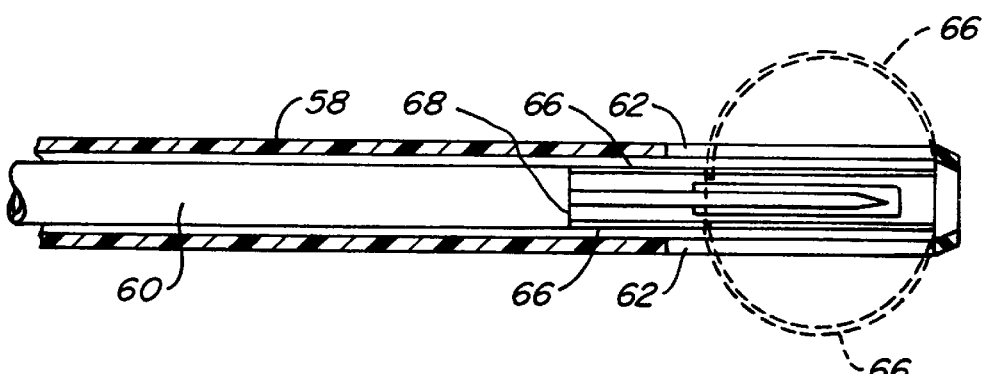
FIG. 7 is a detailed, cross-sectional view taken along line 7—7 of FIG. 5, shown with a pair of vessel-spreading elements in a non-deployed configuration (solid line) and a deployed configuration (broken line).

A pair of penetrating electrode members 70 are also attached to the distal end of the inner member 60, and are further aligned in the opposed slots 64, as best observed in FIG. 6. As the inner member 60 is distally translated, the electrodes 70 will pass outwardly through the slots 64 and forwardly of the distal end of the outer sheath 58, as shown in broken line in FIG. 6.

Figure 8:
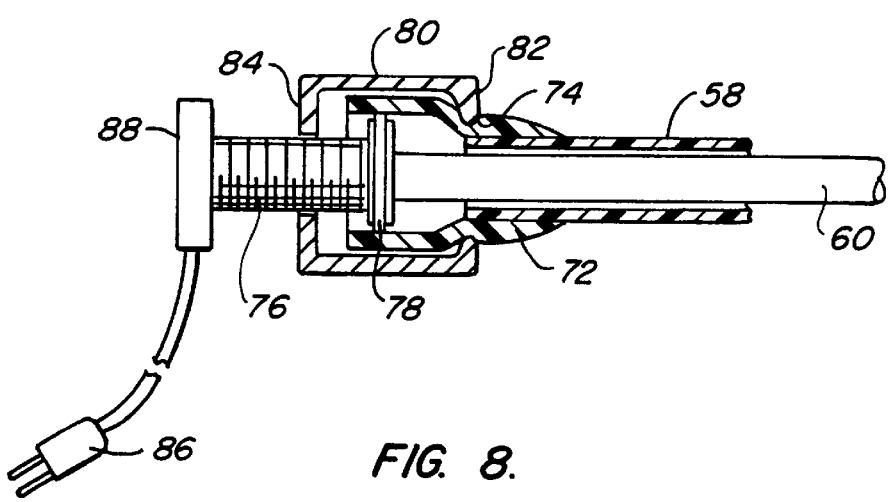
FIG. 8 is a detailed view of the proximal end of the device of FIG. 5, shown in section.

Structure for axially translating an inner member 60 relative to outer sheath 58 is located at the proximal end 54 of the device 50 and is illustrated in FIG. 8. A flared proximal hub 72 is attached and hermetically sealed to the proximal end of outer sheath 58 and includes a circumferential detent 74. A threaded region 76 is provided at the proximal end of the inner member 60, and sealing between the inner member 60 and outer sheath 58 is provided by an o-ring 78. Thus, the inner member 60 can be axially reciprocated relative to the outer sheath 58. Control of the reciprocation is provided by a collar 80 which has a flange 82 received in detent 74 and a threaded follower 84 secured over the threaded region 76. Thus, by rotating the collar 80 relative to both the inner member 60 and outer sheath 58, axial translation of the inner member will be effected. An electrical connector 86 is provided on a cap 88 at the proximal end of the inner member 60. The connector 86 permits connection of the electrodes 70 to a conventional electrosurgical power supply.

Figure 9A:
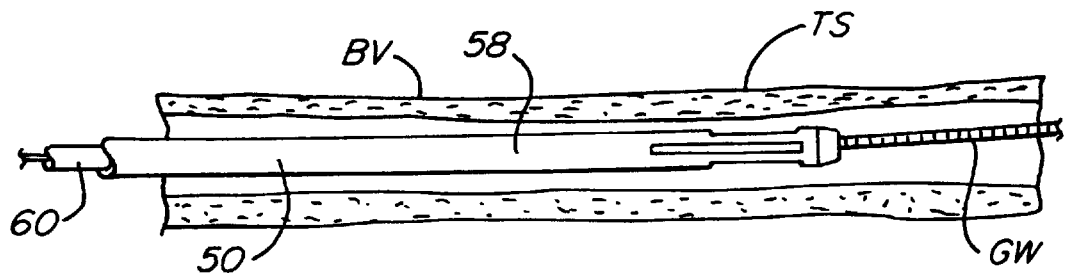
FIGS. 9A–9C illustrate use of the device of FIG. 5 in a method for occluding a blood vessel according to the principles of the present invention.
Figure 9B:
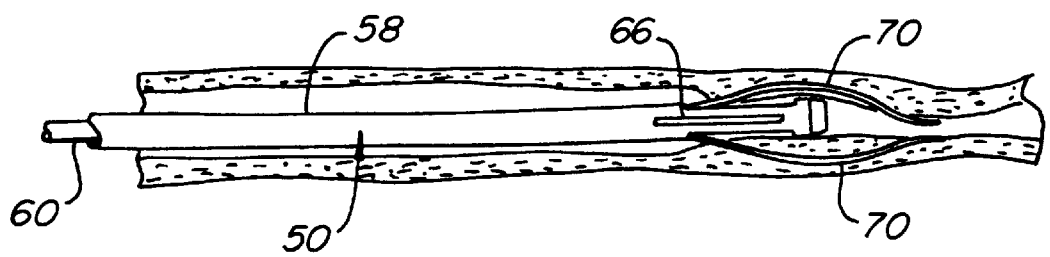
Figure 9C:
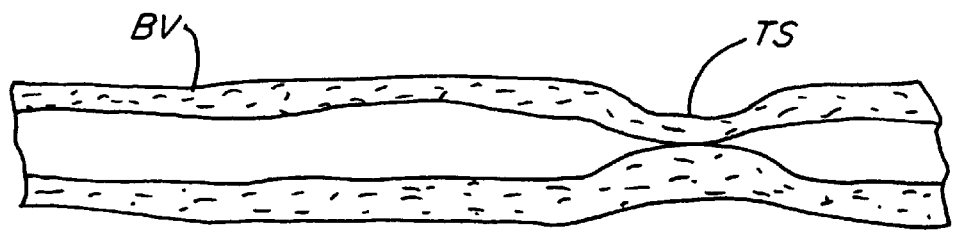
Figure 10:
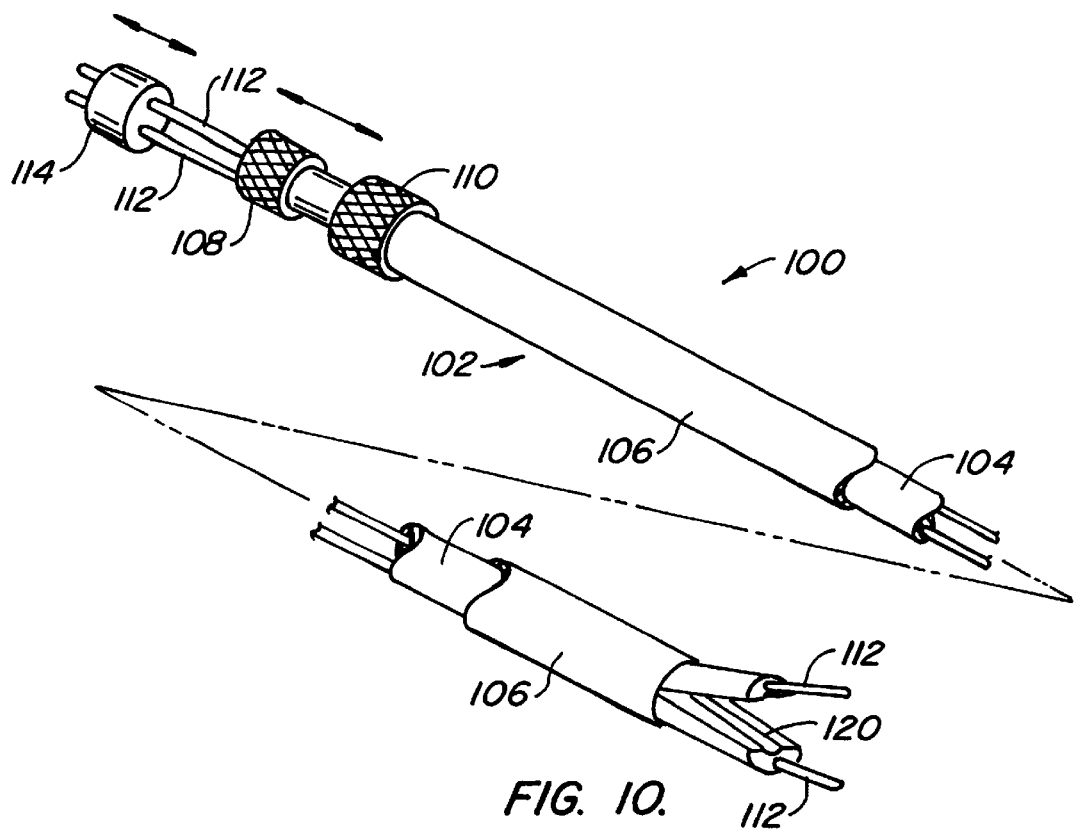
FIG. 10 is a perspective view of a third embodiment of a lumen occlusion device constructed in accordance with the principles of the present invention.

Use of the lumen occlusion device 50 is illustrated in FIGS. 9A–9C. The device 50 is introduced to a target site TS in a blood vessel BV over a guide wire GW in a conventional manner, as illustrated in FIG. 9A. The guide wire is optionally withdrawn, and the inner member 60 distally translated relative to the outer sheath 58, as illustrated in FIG. 9B. The vessel lumen is mechanically collapsed (flattened to pinch the lumen) by expansion of the opposed members 66, and the penetrating electrodes 70 pass subsequently through the epithelial wall of the blood vessel, as illustrated in FIG. 9B. By applying radiofrequency current in the manner described previously, the occlusion region between the collapsed vessel walls can be occluded, as illustrated in FIG. 9C.

In device 50, motion of the spreadable elements 66 is coupled to that of the electrodes 70. This simplifies construction since only a single inner member 60 is required to actuate both components. It will also be possible to decouple actuation of the spreadable elements and the electrodes by providing a separate (non-linked) actuation mechanism for each.

A third embodiment 100 of the occlusion device of the present invention is illustrated in FIGS. 10 and 11A–11C. The device 100 comprises a flexible catheter body 102 including an inner member 104 and outer sheath 106. The inner member 104 and outer sheath 106 are axially reciprocatable relative to one another, and include finger grips 108 and 110, respectively. A pair of penetrating electrodes 112 are reciprocatably mounted in the inner member 104 and attached to connector assembly 114 at their proximal ends.

Figure 11A:
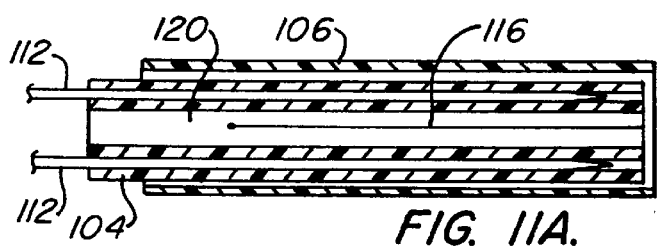
FIGS. 11A–11C are detailed views of the distal end of the device of FIG. 10, shown with a reciprocatable jaw assembly in a retracted configuration (FIG. 11A), an open configuration (FIG. 11B), and an open configuration with penetrating elements extended (FIG. 11C).
Figure 11B:
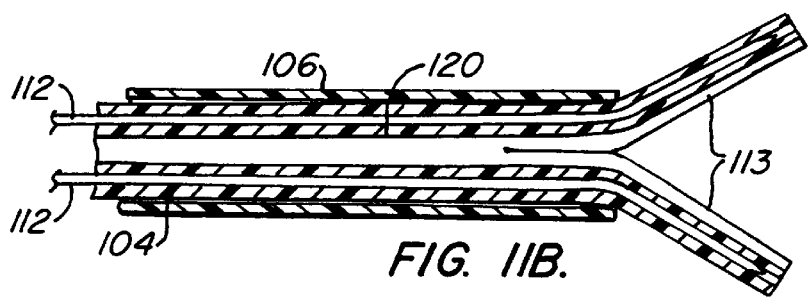
Figure 11C:
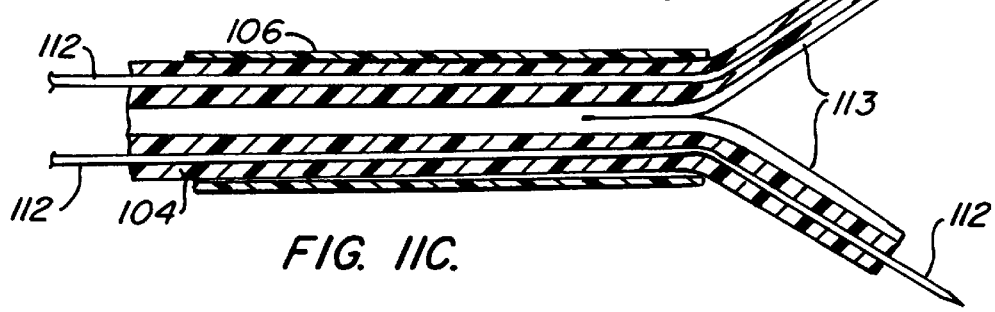

The distal end of the lumen occlusion device is best shown in FIGS. 11A–11C. The inner member 104 is axially split along a line 116 and is treated or spring-loaded to have mechanical "memory" so that it will spread apart when advanced distally relative to the outer sheath 106, as shown in FIG. 11B. Thus, the distal end of the inner member 104 forms a selectively reciprocating "jaw" mechanism, where the jaws open and close by axially sliding the inner member within the outer sheath 106. A central lumen 120 is provided in the inner member 104 to permit the device 100 to be introduced over a guide wire in a conventional manner. After the jaw assembly is opened, as shown in FIG. 11B, the penetrating electrode members 112 may be axially advanced by pushing connector 14 in the distal direction, as illustrated in FIG. 11C.

Figure 12A:
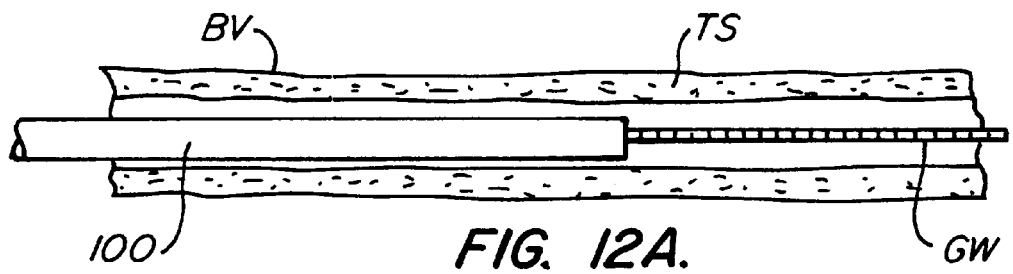
FIGS. 12A–12E illustrate use of the device of FIG. 10 in a method for occluding a blood vessel according to the principles of the present invention.
Figure 12B:
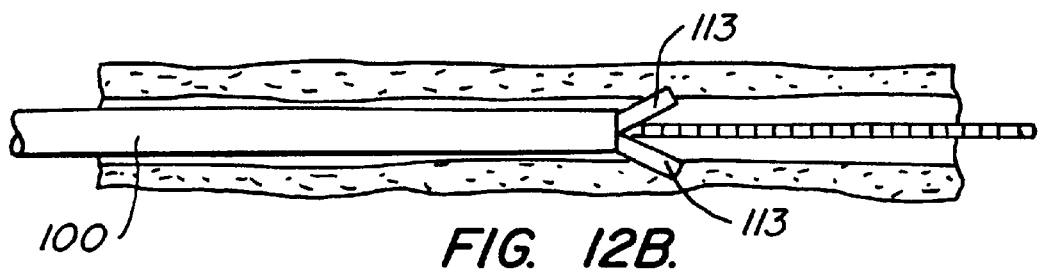
Figure 12C:
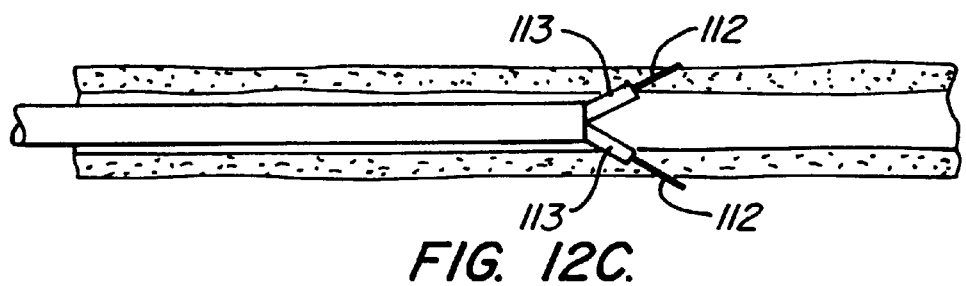
Figure 12D:
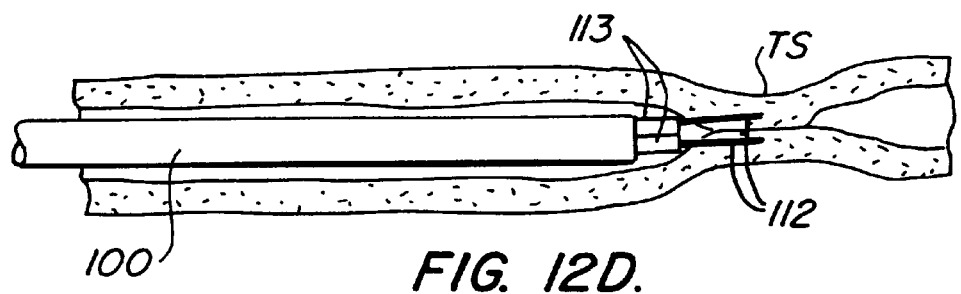
Figure 12E:
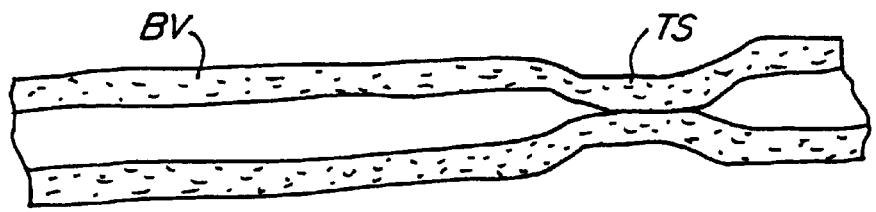

Referring now to FIGS. 12A–12E, use of the device 100 to occlude a blood vessel BV at a target site TS will be described. The device 100 is introduced over a guide wire GW so that its distal end lies at the target site, as illustrated in FIG. 12A. The inner member 104 is then reciprocated distally relative to the outer sheath, opening opposed jaws 113, as illustrated in FIG. 12B. The penetrating distal ends of electrodes 112 are then advanced into opposed sections of the blood vessel wall, as illustrated in FIG. 12C. The jaw members 113 are then closed by at least partially advancing the outer sheath 106 over the inner member 103, as shown in FIG. 12D, to pinch the vessel closed between the electrodes 112. The vessel can then be occluded by passing bipolar radiofrequency current through the collapsed region of the blood vessel, resulting in the occlusion shown at the target site TS in FIG. 12E.

Figure 13A:
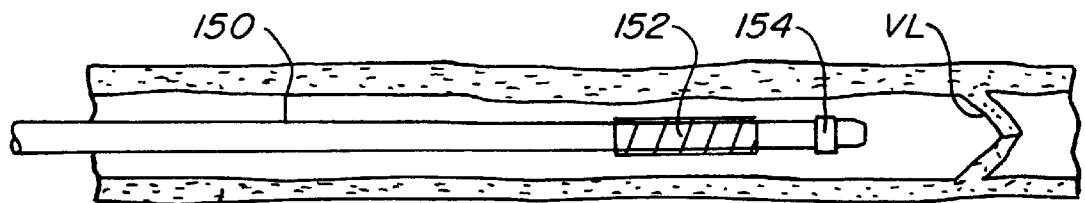
FIGS. 13A–13D illustrate a fourth embodiment of a lumen occlusion device constructed in accordance with the principles of the present invention, and use of that device in a method for occluding a blood vessel according to the principles of the present invention.
Figure 13B:
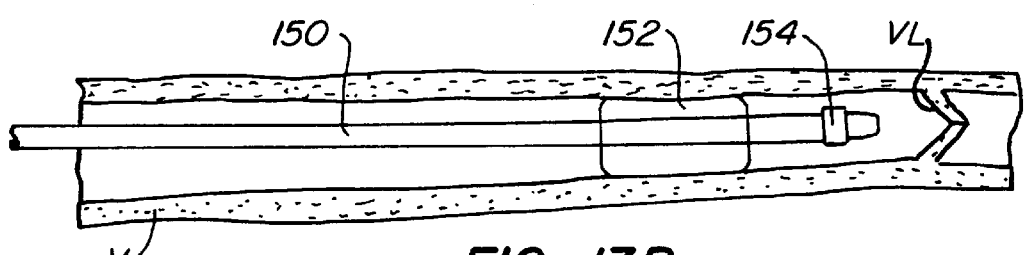
Figure 13C:
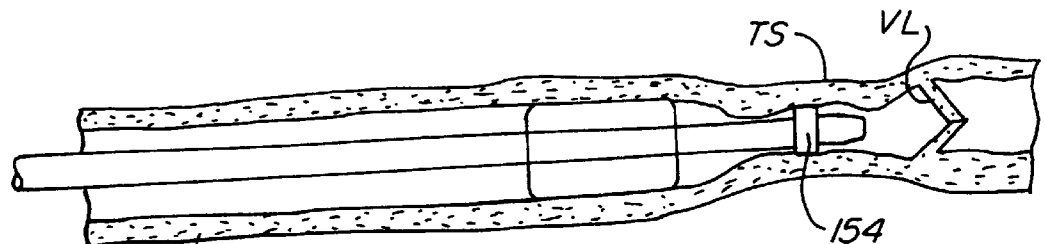
Figure 13D:
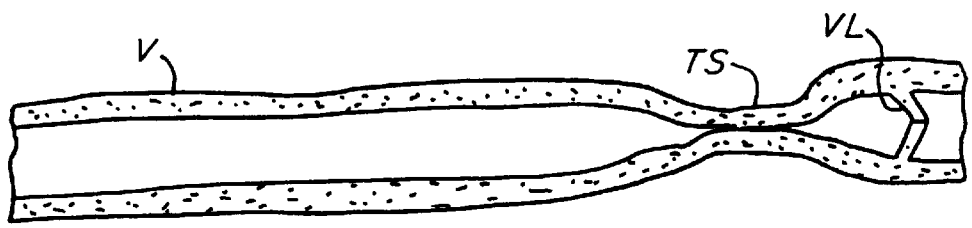

A fourth embodiment 150 of the lumen occlusion device of the present invention is illustrated in FIGS. 13A–13D. The lumen occlusion device 150 is particularly useful for the occlusion of veins V upstream of a valve VL, as shown in FIG. 13A. The device 150 includes an inflatable balloon 152 which is shown in its non-inflated condition in FIG. 13A. The device further includes an electrode 154 which is located distally of the occlusion balloon 152. By inflating balloon 152 upstream of the valve VL, as illustrated in FIG. 13B, a region of quiescent blood is created between the balloon 152 and the valve VL. A negative pressure can then be drawn through the catheter body, causing a collapse of the vein in region TS, as illustrated in FIG. 13C. Monopolar RF energy can then be delivered through the electrode 154 to occlude the vein, as illustrated in FIG. 13D. Alternatively, the device 150 may be used to deliver bipolar RF current by using a guide wire (or other thin wire electrode) extending from the distal tip of the device. Use of the guide wire will cause clotting distally of the device tip, where such clot is less likely to be disrupted by withdrawal of the catheter.

Although the foregoing invention has been described in some detail by way of illustration and example, for purposes of clarity of understanding, it will be obvious that certain changes and modifications may be practiced within the scope of the appended claims.

What is claimed is:

1. A lumen occlusion device, said device comprising:

a shaft having a proximal end and a distal end;

means at the distal end of the shaft for selectively engaging opposed portions of an interior wall of a lumen and for drawing opposed portions of the wall together over an occlusion region, wherein said opposed portions are positioned across the lumen from each other; and means on the shaft for injuring the drawn together opposed wall portions over the occlusion region, so as to cause the drawn together opposed wall portions to fuse thereby to occlude the lumen.

2. A lumen occlusion device as in claim 1, wherein the shaft comprises a flexible body having dimensions suitable for introduction to a patient's vasculature.

3. A lumen occlusion device as in claim 2, wherein the flexible body has an outer diameter in the range from 1 mm to 5 mm and a length in the range from about 40 cm to 200 cm.

4. A lumen occlusion device as in claim 1, wherein the engaging and drawing means comprises a pair of opposed selectively openable and closeable elements configured to engage and penetrate into the opposed wall portions when in an open condition and to draw together said wall portions when moved into a closed condition.

5. A lumen occlusion device as in claim 4, wherein said opposed elements are pivotally mounted at the distal end of the shaft.

6. A lumen occlusive device as in claim 5, wherein said pivotally mounted opposed elements comprise a pair of jaws and a reciprocatably mounted pin on each jaw, wherein the pins comprise electrodes which are connectable to an external radiofrequency power supply for injuring the opposed wall portions together.

7. A lumen occlusion device as in claim 1, wherein the engaging and drawing means comprises a pair of opposed spreading elements for selectively engaging and spreading apart a first pair of opposed wall portions to cause a second pair of opposed wall portions of the lumen to close along a transverse line defined by said elements.

8. A lumen occlusion device as in claim 7, wherein said injuring means comprises at least two electrodes engageable with the opposed wall portions when the lumen is closed by the spreading elements.

9. A lumen occlusion device as in claim 1, wherein the engaging and drawing means comprises a balloon near the distal end of the shaft for temporarily occluding the lumen and an aspiration lumen in the shaft for drawing negative pressure through the shaft collapsing the wall when occluded by the balloon.

10. A lumen occlusion device as in claim 9, wherein the injuring means comprises at least one electrode extendable from the distal end of the shaft.

11. A lumen occlusion device including:

an elongate shaft having a distal end portion defining a distal end, the distal end portion being dimensioned to be insertable into and along a lumen having a lumen wall;

a deformation structure near the distal end of the shaft, the deformation structure being arranged to selectively draw together opposed interior wall portions of the lumen wall, which portions face one another across the lumen, together; and a selectively activatable injury structure being arranged to injure the opposed wall portions when drawn together, so as to cause the opposed wall portions to fuse together thereby to occlude the lumen.

12. A lumen occlusion device as in claim 11, wherein the deformation structure includes at least one member selectively displaceable between a collapsed condition, in which the member is positioned closely adjacent the distal end portion of the shaft, and a deployed condition, in which the member is displaced laterally outwardly of the shaft, and, in which, a laterally outermost region of the member engages the lumen wall.

* * * * *

UNITED STATES PATENT AND TRADEMARK OFFICE
CERTIFICATE OF CORRECTION

PATENT NO. : 6,077,261
DATED : June 20, 2000
INVENTOR(S) : Robert S. Behl et al.

It is certified that error appears in the above-identified patent and that said Letters Patent is hereby corrected as shown below:

On the title page: Item

[54] METHOD AND DEVICE FOR PERMANENT VESSEL OCCLUSION

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.     : 6,077,261
DATED          : June 20, 2000
INVENTOR(S)    : Robert S. Behl et al.

It is certified that error appears in the above-identified patent and that said Letters Patent is hereby corrected as shown below:

Title page, Item [54] and Column 1, lines 1 and 2,
The title should read as follows: -- [54] METHOD AND DEVICE FOR PERMANENT VESSEL OCCLUSION --.

Signed and Sealed this

Fifteenth Day of October, 2002

*Attest:*

JAMES E. ROGAN
*Attesting Officer*      *Director of the United States Patent and Trademark Office*